(12) United States Patent
Anwar et al.

(10) Patent No.: US 9,066,871 B2
(45) Date of Patent: Jun. 30, 2015

(54) SODIUM-HYPOCHLORITE-BASED BODY WASH COMPOSITIONS

(75) Inventors: Azam Anwar, Dallas, TX (US); Clay J. Cockerell, Dallas, TX (US); Catherine Sitbon, Westwood, NJ (US)

(73) Assignee: TopMD, Inc., Dallas, TX (US)

( * ) Notice: Subject to any disclaimer, the term of this patent is extended or adjusted under 35 U.S.C. 154(b) by 0 days.

(21) Appl. No.: 13/446,392

(22) Filed: Apr. 13, 2012
(Under 37 CFR 1.47)

(65) Prior Publication Data

US 2013/0089628 A1   Apr. 11, 2013

Related U.S. Application Data (60) Provisional application No. 61/476,067, filed on Apr. 15, 2011, provisional application No. 61/532,444, filed on Sep. 8, 2011.

(51) Int. Cl.
| | | |
|---|---|---|
| A61K 33/14 | (2006.01) | |
| A61K 8/20 | (2006.01) | |
| A61K 8/42 | (2006.01) | |
| A61K 8/44 | (2006.01) | |
| A61K 8/46 | (2006.01) | |
| A61Q 17/00 | (2006.01) | |
| A61Q 19/10 | (2006.01) | |
| A61K 33/20 | (2006.01) | |
| A61K 8/02 | (2006.01) | |

(52) U.S. Cl.
CPC ... *A61K 8/20* (2013.01); *A61K 8/42* (2013.01); *A61K 8/442* (2013.01); *A61K 8/463* (2013.01); *A61Q 17/005* (2013.01); *A61Q 19/10* (2013.01); *A61K 33/20* (2013.01); *A61K 8/44* (2013.01); *A61K 8/0208* (2013.01); *A61K 2800/596* (2013.01)

(58) Field of Classification Search
CPC ........... A61K 8/20; A61K 8/42; A61K 8/442; A61K 8/463; A61K 8/44; A61K 8/0208; A61K 33/20; A61K 2800/596; A61Q 17/005; A61Q 19/10
See application file for complete search history.

(56) References Cited

U.S. PATENT DOCUMENTS

| | | |
|---|---|---|
| 4,376,787 A | 3/1983 | Lentsch et al. |
| 4,737,307 A | 4/1988 | Brown et al. |
| 5,273,678 A | 12/1993 | Deroux et al. |
| 5,427,801 A | 6/1995 | Uehara |
| 6,387,384 B1 | 5/2002 | Probert et al. |
| 6,544,401 B1 | 4/2003 | Colic |
| 6,589,568 B2 | 7/2003 | Camper et al. |
| 7,056,538 B2 | 6/2006 | Pinza et al. |
| 2005/0107272 A1* | 5/2005 | Pinzon et al. .............. 510/130 |
| 2007/0232694 A1 | 10/2007 | Phillips |
| 2008/0132438 A1 | 6/2008 | Hoffman et al. |
| 2009/0274772 A1 | 11/2009 | Bowker |
| 2010/0284951 A1 | 11/2010 | Pongprapansiri et al. |
| 2011/0052506 A1 | 3/2011 | Abel et al. |
| 2011/0288360 A1* | 11/2011 | Puckett et al. .............. 588/299 |

FOREIGN PATENT DOCUMENTS

| | | |
|---|---|---|
| FR | 2920975 | 3/2009 |
| WO | 2007070861 A1 | 6/2007 |
| WO | 2008157847 A1 | 12/2008 |

OTHER PUBLICATIONS

International Search Report and Written Opinion, dated Sep. 4, 2012 for PCT Application No. PCT/US2012/033510, 10 pages.

* cited by examiner

*Primary Examiner* — Lezah Roberts
*Assistant Examiner* — Nannette Holloman
(74) *Attorney, Agent, or Firm* — Winstead PC (57) ABSTRACT

Sodium hypochlorite-based compositions that are non-toxic and have antimicrobial and cleansing properties may include from about 0.025% to about 10% by weight of sodium hypochlorite. For example, the compositions may include less than 1% by weight of sodium hypochlorite (e.g., less than 0.5% by weight of sodium hypochlorite). The compositions may further include sodium laureth sulfate, cocamidopropyl betaine, cocamide MEA, disodium EDTA, and deionized water. Such compositions may be applied externally to a mammalian body through rinse-off or leave-on applications. Compositions also may be incorporated as a component of other products, such as deodorants, towelettes, or powders.

4 Claims, 11 Drawing Sheets

SODIUM-HYPOCHLORITE-BASED BODY WASH COMPOSITIONS

This application claims the benefit of U.S. Provisional Patent Application Nos. 61/476,067, filed Apr. 15, 2011, and 61/532,444, filed Sep. 8, 2011. The entire contents of these references are incorporated herein by reference.

FIELD OF THE INVENTION

This disclosure relates generally to antimicrobial and cleansing compositions and methods, and more specifically, to sodium hypochlorite-based compositions having antimicrobial and cleansing properties.

BACKGROUND

In the past, sodium hypochlorite has been used in various applications, including household cleaners, chlorination of drinking water, chlorination of swimming pools, bleaching of cloth, and controlling bacteria and slime in industrial water. Sodium hypochlorite is a powerful oxidizing agent. Accordingly, at higher doses, it has a tendency to often rapidly produce burns when in contact with skin. Further, sodium hypochlorite may be unstable when exposed to heat, light, and/or air. Therefore, despite its disinfectant qualities, sodium hypochlorite has been undesirable for usages that may involve application to skin.

SUMMARY

In general, the present disclosure is directed to sodium hypochlorite-based compositions that have antimicrobial and cleansing properties and are generally non-toxic to humans or other mammalians. The present disclosure is also generally directed to a method of making and using such sodium hypochlorite-based compositions. Example compositions as described herein may be suitable for application to parts of a mammalian body such as, e.g., a human body, a cat body, a dog body, a horse body, or the like.

Compositions according to embodiments of the present disclosure may include sodium hypochlorite in combination with additional components that make the sodium hypochlorite suitable for applying to mammalian body parts (e.g., skin). Examples of such additional components include a foaming agent and/or a foam boosting agent and/or a viscosity enhancing agent and/or a chelating agent and/or a solvent. In one example, a composition comprises (or, optionally, consists essentially of, or consists of) sodium hypochlorite in combination with a solvent and an anionic surfactant that functions as a foaming agent. The anionic surfactant may be, e.g., sodium laureth sulfate, and the solvent be water (e.g., deionized water). The composition may also include (or, optionally, consist essentially of, or consist of) a nonionic surfactant that functions to enhance viscosity such as, e.g., coconut monoethanolamide, which can be referred to as cocamide MEA. In addition, in some examples, the composition may further include (or, optionally, consist essentially of, or consist of) an amphoteric surfactant that functions to enhance or boost the foaming properties of the anionic surfactant. An example of an amphoteric surfactant is cocamidopropyl betaine. Additional components that may be incorporated into the composition include chelating agents, stabilizing agents, and the like. For example, the composition may further include (or, optionally, consist essentially of, or consist of) a chelating agent that binds free radicals and impurities such as, e.g. disodium ethylenediaminetetraacetic acid, which can be referred to as disodium EDTA, or calcium disodium EDTA.

In one example according to the disclosure, a composition is described that includes (or, optionally, consist essentially of, or consist of) sodium laureth sulfate, cocamidopropyl betaine, cocamide MEA, disodium EDTA, calcium disodium EDTA, sodium hypochlorite, and deionized water. In this example, sodium laureth sulfate may comprise from approximately 3 wt % to approximately 40% wt % (e.g., from approximately 5 wt % to approximately 25% wt %, or from approximately 7 wt % to approximately 15 wt %) of the resultant composition, where the weight percentage is based on the overall weight of the composition (i.e., after combining all constituent components). It is noted that the wt % of sodium laureth sulfate may be considered the weight percentage of the active sodium laureth sulfate molecule, since a person of ordinary skill in the art is well aware that sodium laureth sulfate is generally found in a diluted form. The resultant composition may also include from approximately 0.5 wt % to approximately 7 wt % cocamidopropyl betaine (e.g., from 3.75 wt % to 4.25 wt %, or approximately 4.0 wt %), from approximately 1 wt % to approximately 7 wt % cocamide MEA (e.g., from 3.25 wt % to 3.75 wt %, or approximately 3.5 wt %), from approximately 0 wt % to approximately 3 wt % disodium EDTA or calcium disodium EDTA (e.g., approximately 0.10 wt % to approximately 0.40 wt %), and from approximately 0.025 wt % to approximately 10 wt % sodium hypochlorite (e.g., from approximately 0.1 wt % to approximately 2 wt %). The remainder of the resultant composition may be water (e.g., deionized water).

The percentage by weight of sodium hypochlorite incorporated into compositions according to embodiments of the present disclosure may be driven by whether such compositions are to be rinsed off following application or if they are to be left on the skin or other body parts without rinsing (i.e., leave-on applications). In various examples, the amount of sodium hypochlorite in the composition may range from 0.025 wt % to 10 wt % such as, e.g., from 0.1 wt % to 2 wt %, from 0.15 wt % to 0.75 wt %, from 0.2 wt % to 0.5 wt %, or from 0.3 wt % to 0.4 wt %.

Sodium hypochlorite-based compositions as described herein may exhibit antimicrobial properties and/or anti-inflammatory properties and/or cleansing properties. The compositions may be delivered to an end user in a variety of forms. Such forms may include body wash, shampoo, creams, lotions, gels, sprays, foams, pads, films, patches, wipes, swabs, deodorants, powders, and solutions. These compositions may be stand-alone products or they may be incorporated as a component of another product, such as deodorants or foot powders.

Sodium hypochlorite-based compositions according to the disclosure can be prepared using any suitable method. Methods for preparation of sodium hypochlorite-based compositions having antimicrobial properties according to some embodiments of the present disclosure may include combining sodium laureth sulfate, cocamidopropyl betaine, cocamide MEA, disodium EDTA or calcium disodium EDTA, and deionized water to form a first mixture. The first mixture may be heated, e.g., to a temperature ranging from approximately 65° C. to approximately 75° C. to ensure uniformity of the mixture. As each component of the first mixture is added, the components may be mixed with light agitation between additions. The first mixture may then be cooled, e.g., to a temperature below 37° C. such as a temperature ranging from approximately 25° C. to approximately 35° C., and a viscosity of approximately 3,000 to approximately 50,000 cps.

Upon reaching the desired temperature range and viscosity parameters, a mixture of sodium hypochlorite and deionized water may be introduced into the first mixture to form sodium hypochlorite-based compositions according to embodiments of the present disclosure. When adding sodium hypochlorite and deionized water to the first mixture, side-sweep agitation may be used to avoid aeration of the sodium hypochlorite-based composition when formed. Sodium hypochlorite-based compositions formed according to embodiments of the present disclosure may have a thick, gel-like viscosity.

Sodium hypochlorite-based compositions formed using methods according to embodiments of the present disclosure may be delivered to an end user through various mechanisms that limit the composition's exposure to heat, light and/or air prior to use. For example, opaque sealed bottles or airless dispensers that may include a self-sealing actuator may be used to dispense such compositions. The composition may be dispensed, for example, onto a user's hand, directly onto an area of a body to be treated, or onto a cloth, such as a washcloth or a towelette, as a means to transport the composition to area(s) of the body to be treated. In other embodiments of the present disclosure, the composition may be impregnated into carrier means such as a towelette or wipe. When the composition is impregnated into carrier means, the carrier means may be sealed in a container that does not react adversely with the composition prior to use and that prevents the composition from being exposed to light, heat and/or light prior to use.

In one example, a body wash composition is described that includes from 0.1 wt % to 10 wt % of an alkali metal or alkaline earth metal hypochlorite, an anionic surfactant that includes an alkyl sulfate, a nonionic surfactant that includes an alkonolamide, an amphoteric surfactant, and a chelating agent.

In another example, a body wash system is described that includes a body wash composition and a body wash dispensing device. According to the example, the body wash composition includes from 0.1 wt % to 10 wt % of an alkali metal or alkaline earth metal hypochlorite, an anionic surfactant that includes an alkyl sulfate, a nonionic surfactant that includes an alkonolamide, an amphoteric surfactant, and a chelating agent.

In another example, a method is described that includes applying a body wash composition to skin of a mammalian body. According to the example, the body wash composition including from 0.1 wt % to 10 wt % of an alkali metal or alkaline earth metal hypochlorite, an anionic surfactant that includes an alkyl sulfate, a nonionic surfactant that includes an alkonolamide, an amphoteric surfactant, and a chelating agent.

In another example, a body wash composition is described that consists essentially of from 0.1 wt % to 10 wt % of an alkali metal or alkaline earth metal hypochlorite, an anionic surfactant that functions as a foaming agent and that includes an alkyl sulfate, a nonionic surfactant that functions as a viscosity enhancing agent and that includes an alkonolamide, an amphoteric surfactant that functions as a foam boosting agent, and a chelating agent.

The details of one or more examples are set forth in the accompanying drawings and the description below. Other features, objects, and advantages will be apparent from the description and drawings, and from the claims.

DETAILED DESCRIPTION

The present disclosure provides, in some examples, for sodium hypochlorite-based compositions that have antimicrobial properties and may be non-toxic when applied to the human body. Sodium hypochlorite-based compositions according to embodiments of the present disclosure may be water-based to feel wet when contacted with parts of the body. More specifically, compositions according to some embodiments of the present disclosure may be comprised of sodium laureth sulfate, cocamidopropyl betaine, cocamide MEA, disodium EDTA or calcium disodium EDTA, sodium hypochlorite, and deionized water. Depending on the materials included in the sodium hypochlorite-based compositions, the sodium hypochlorite-based compositions may foam and lather in response to physical washing action. This foaming and lathering can provide a cleansing effect, for example, helping to remove loose debris, blood, fecal material, or the like from the skin of the patient to which the sodium hypochlorite-based composition is applied.

Sodium hypochlorite may be present in compositions according to embodiments of the present disclosure in an amount effective to provide antimicrobial properties sufficient to kill or inhibit the growth of microorganisms and/or in an amount effective to provide anti-inflammatory relief when applied to inflamed tissue and/or in an amount effective to provide antiviral properties sufficient to kill or inhibit the growth viruses and/or in an amount effective to provide anti-fungal properties. Example disease states that the compositions may kill or inhibit the growth of include, e.g., acne, folliculitis, atopic dermatitis, skin infection, colonization, and psoriasis. Example bacteria that the compositions may kill or inhibit the growth of include, but are not limited to, *staphylococcus aureus* and *propionibacterium* acnes. An example virus the compositions may kill or inhibit the growth of is *molluscum contagiosum*. As another example, the compositions may kill or inhibit the growth of ringworm caused by a fungus. However, compositions including sodium hypochlorite may be sufficiently diluted and placed in combination with other components so as to be non-toxic to humans or other mammalians that may use such compositions.

Sodium hypochlorite-based compositions according to embodiments of the present disclosure may include from approximately 0.025 wt % to approximately 10 wt % sodium hypochlorite such as, e.g., from approximately 0.1 wt % to approximately 2 wt % sodium hypochlorite, from approximately 0.15 wt % to approximately 0.75 wt % sodium hypochlorite, from approximately 0.2 wt % to approximately 0.5 wt % sodium hypochlorite, or from approximately 0.3 wt % to approximately 0.4 wt % sodium hypochlorite. In some embodiments, the sodium hypochlorite-based compositions include less than 1 wt % sodium hypochlorite such as, e.g., less than 0.5 wt % sodium hypochlorite, or less than 0.35 wt % sodium hypochlorite. The percentage by weight of sodium hypochlorite in such compositions may be adjusted using water. It should be appreciated that the percentage of sodium hypochlorite incorporated into some compositions according to the present disclosure may be relative low, e.g., at or below about 1 wt %, in order to minimize or even to avoid a strong odor generally characteristic of sodium hypochlorite.

Compositions according to the disclosure may include any suitable concentration of sodium hypochlorite. As examples, a composition may include approximately 5.5 wt % sodium hypochlorite, approximately 2.0 wt % sodium hypochlorite, approximately 1.0 wt % sodium hypochlorite, approximately 0.45 wt % sodium hypochlorite, approximately 0.35 wt % sodium hypochlorite, approximately 0.25 wt % sodium, or approximately 0.025 wt % sodium hypochlorite, although different concentrations are both possible and contemplated. In some examples, the amount of sodium hypochlorite incorporated into a specific composition may be selected based on the intended use of the specific composition. For example, the percentage of sodium hypochlorite included in some embodiments of the present disclosure may be relatively low (e.g., less than approximately 0.1 wt %, or approximately 0.025 wt %) if the composition is intended to be applied to and not rinsed off the skin (i.e., a leave-on application). Conversely, the percentage of sodium hypochlorite may be higher (e.g., greater than approximately 0.15 wt %, from approximately 0.15 wt % to approximately 1 wt %) if the composition is intended to be used in a rinse-off application. In addition, the percentage of sodium hypochlorite may be altered in order to provide a variety of strengths of rinse-off products, such as full strength, regular strength, and mild strength, to address user sensitivity. Further, varying percentages of sodium hypochlorite may be used depending on whether the resultant composition may be used as a standalone product, such as a body wash, or may be otherwise incorporated as a component within another product, including but not necessarily limited to, deodorants and foot powders.

While compositions according to the present disclosure are generally described as including sodium hypochlorite as an antimicrobial and/or anti-inflammatory agent, it should be appreciated that the compositions may include other antimicrobial and/or anti-inflammatory agents in addition to or in lieu of sodium hypochlorite and the disclosure is not limited in this respect. For example, the compositions may include any alkali metal or alkaline earth metal hypochlorite and the disclosure is not limited to the specific example of sodium hypochlorite.

Compositions according to embodiments of the present disclosure also may comprise at least one foaming agent. Inclusion of a foaming agent in sodium hypochlorite-based compositions may enhance the delivery and application of the composition. Accordingly, less of the composition by weight may be needed to cover a larger area of the body to be treated. Foaming agents also may boost or enhance foam that may be produced, thereby adding body or viscosity to the resultant composition. Such compositions may lather or foam when applied directly to the body, when applied to a cloth or towelette, or when rubbed between the hands and then applied to parts of the body.

The at least one foaming agent may be an anionic surfactant such as, e.g., an alkyl sulfate, an alkyl ether sulfate, or the like. Example alkyl sulfates include sodium lauryl sulfate, triethanol amine (TEA) lauryl sulfate, ammonium lauryl sulfate, and the like. Example alkyl ether sulfates include sodium lauryl ether sulfate (also known as sodium laureth sulfate), and the like. Anionic surfactants may be used as detergents as they generally have good solubility and are generally mild when applied to skin. In one example, the sodium hypochlorite-based composition includes sodium laureth sulfate. Although sodium laureth sulfate may generally be considered an irritant, its presence in compositions according to embodiments of the present disclosure has generally not been found to cause adverse irritation when applied to a body part (e.g., human skin). In some examples, an anionic surfactant (e.g., sodium laureth sulfate) may comprise from approximately 3 wt % to approximately 40 wt % such as, e.g., from approximately 5 wt % to approximately 25 wt %, from approximately 6 wt % to approximately 15 wt %, or from approximately 7 wt % to approximately 10 wt % of the resultant composition, where the weight percentage is based on the overall weight of the composition (i.e., after combining all constituent components). It is noted that the wt % of sodium laureth sulfate may be considered the weight percentage of the active sodium laureth sulfate molecule, since a person of ordinary skill in the art is well aware that sodium laureth sulfate is generally found in a diluted form. While sodium laureth sulfate has been described, other foaming agents, including other anionic surfactants, may be incorporated into compositions without departing from the present disclosure.

In some embodiments, the sodium hypochlorite-based composition includes a nonionic surfactant in addition to the at least one anionic surfactant that functions as foaming agent. The nonionic surfactant may provide, among other properties, viscosity-enhancing properties. An example nonionic surfactant is an alkonolamide such as, e.g., coconut monoethanolamide, which also may be referred to by the INCI name, cocamide MEA. Cocamide MEA may be included in such compositions because of its excellent viscosity-enhancing and foam-boosting and stabilization properties. While cocamide MEA may be included as a foaming agent in compositions according to embodiments of the present disclosure, it should be appreciated that it also may act as an emulsifier, lubricant agent, thickening agent, as well as a wetting agent in such compositions. Further, in different examples, the composition may include a nonionic surfactant different than cocamide MEA. Examples of different nonionic surfactants include cocamide diethanolamide (i.e., cocamide DEA), lauramide MEA, and lauramide DEA, although other components are possible.

In embodiments in which the sodium hypochlorite-based composition includes a nonionic surfactant, the nonionic surfactant (e.g., cocamide MEA) may be present in the composition in any suitable weight percentage. In some examples, concentrations of the nonionic surfactant greater than approximately 4.0 wt % may cause the composition to become lumpy and highly viscous, making the composition difficult to use for some applications. For this reason, the sodium hypochlorite-based composition in these examples may include less than approximately 4.0 wt % of the nonionic surfactant such as, e.g., less than approximately 3.75 wt %, or less than approximately 3.5 wt %. In other examples, the sodium hypochlorite-based composition may include from approximately 1.0 wt % to approximately 7.0 wt % of the nonionic surfactant such as, e.g., from 3.25 wt % to 3.75 wt %, or approximately 3.5 wt % of the nonionic surfactant. It should be appreciated, however, that the percentage of the nonionic surfactant that may be included in compositions according to embodiments of the present disclosure may vary depending on whether the viscosity of the composition may need adjustment, e.g., prior to addition of sodium hypochlorite as described in more detail below.

Amphoteric surfactants also may be incorporated into compositions formed according to embodiments of the present disclosure. Amphoteric surfactants may provide thickening and high foam properties to the composition and may provide foam-boosting properties. Lauryl betaine is an example of an amphoteric surfactant that may be incorporated into embodiments of the present disclosure. Cocamidopropyl betaine is another example of an amphoteric surfactant that may be incorporated into embodiments of the present disclosure. Cocamidopropyl betaine is generally considered less of an irritant than other foaming agents or surfactants such as, e.g., sodium laureth sulfate.

In embodiments in which the sodium hypochlorite-based composition includes an amphoteric surfactant, the amphoteric surfactant (e.g., cocamidopropyl betain) may be present in the composition in any suitable weight percentage. In some examples, concentrations of the amphoteric surfactant greater than approximately 7.0 wt % may deactivate the antimicrobial properties of sodium hypochlorite-based composition. For this reason, the sodium hypochlorite-based composition in these examples may include less than approximately 7.0 wt % of the amphoteric surfactant such as, e.g., less than approximately 5.0 wt %, or less than approximately 4.5 wt %. In other examples, the sodium hypochlorite-based composition may include from approximately 0.5 wt % to approximately 7.0 wt % amphoteric surfactant such as, e.g., from 3.75 wt % to 4.25 wt %, or approximately 4.0 wt % amphoteric surfactant. It should be appreciated that other concentrations of an amphoteric surfactant are possible and the disclosure is not necessarily limited in this respect.

Embodiments of a sodium hypochlorite-based composition in accordance with the disclosure may include a chelating agent. A chelating agent may bind to any free radicals or impurities in the composition, thereby allowing the active ingredients of the composition, particularly sodium hypochlorite, to work effectively and consistently on the area of application without excessive chemical disturbance. An example chelating agent that may be incorporated into a composition is disodium ethylenediaminetetraacetic acid, which can be referred to as disodium EDTA or calcium disodium EDTA. Disodium EDTA or calcium disodium EDTA may act as a stabilizer in such compositions as well as a chelating agent. Other example chelating agents include EDTA, trisodium EDTA, and tetrasodium EDTA. In examples in which the composition includes a chelating agent, the chelating agent (e.g., disodium EDTA or calcium disodium EDTA) may be used at levels that are low enough to not cause any direct harm when contacted with any part of a body. While these levels may vary, e.g., based on the specific type of chelating agent and the specific formulation of the composition, in some examples, the composition may include from approximately 0.10 wt % to approximately 0.20 wt % chelating agent.

Sodium hypochlorite-based compositions in accordance with the disclosure may include a variety of other components in addition to or in lieu of the components discussed above. For example, a sodium-hypochlorite based composition may include a humectant such as, e.g., glycerin, propylene glycol, or the like. A humectant may improve the feel of the product during application and may also help improve the shelf stability of the product (e.g., during freezing and thawing cycles). The amount of humectant added to a sodium hypochlorite-based composition may vary, e.g., based on the specific type of humectant utilized. In some examples, a sodium hypochlorite-based composition that includes glycerin may include less than approximately 3.0 wt % glycerin, while a sodium hypochlorite-based composition that includes propylene glycol may include less than approximately 5.0 wt % propylene glycol.

Other enhancing additives may be included in a sodium-hypochlorite based composition in addition to or in lieu of a humectant. Example enhancing additives that may be added to the sodium-hypochlorite based composition include sarcosinates (e.g., sodium lauryl sulfoacetate) and/or amphoterics and/or alkonolamides and/or sulfocuccinates. Additional examples of enhancing additives that may be added to the sodium-hypochlorite based composition include sulphur resorcinol, benzoyl peroxide, salicylic acid. In one example, the body wash composition includes between 0.05 wt % and 10 wt % salicylic acid such as, e.g., between 0.1 wt % and 5 wt %, or between 0.4 wt % and 3 wt % salicylic acid, where the weight percentage is based on the overall weight of the composition (i.e., after combining all constituent components).

Embodiments of the sodium hypochlorite-based compositions may be substantially free of certain components that may be irritating to mammalian (e.g., human) body parts or may be disadvantageous for other reasons. For example, a sodium hypochlorite-based composition in accordance with some examples may be substantially or entirely free of one or more (and optionally all) of the following components: sulphur resorcinol, benzoyl peroxide, salicylic acid, isethionates, olefin sulfonates, taurates, amine oxides, and/or protein-based surfactants. While these components are sometimes found in cleansing products, these components may, in some examples, react with other components in a sodium hypochlorite-based composition so as to reduce the efficacy of the sodium hypochlorite-based composition. For this and other reasons, one or more of the components may be substantially absent from a sodium hypochlorite-based composition formed in accordance with the disclosure.

Methods for preparation of sodium hypochlorite-based compositions having antimicrobial properties according to embodiments of the present disclosure may involve a two-phase method (Phase A and Phase B). In Phase A, all the components of the composition except the sodium hypochlorite (which may be a solution that includes water) may be combined to form a first mixture. For example, in Phase A, sodium laureth sulfate, cocamidopropyl betaine, cocamide MEA, disodium EDTA, and deionized water may be combined to form a first mixture. The relative percentage of each of these components may vary, e.g., as indicated above, based on the intended formulation of the composition.

This first mixture may be heated, e.g., to a temperature from approximately 60° C. to approximately 80° C. such as from approximately 70° C. to 75° C. to help ensure uniformity of the mixture. As components are added to form a first mixture, mixing with light agitation may be used to minimize (e.g., prevent) aeration of the resultant composition. The first mixture may then be cooled to room temperature (e.g., a temperature less than approximately 37° C. such as, e.g., from approximately 25° C. to approximately 35° C., or approximately 30° C.), which may result in a viscosity from approximately 1,000 centipoise (cps) to approximately 30,000 cps.

Upon reaching the desired temperature (generally around room temperature) and viscosity, Phase B, a mixture of sodium hypochlorite and deionized water, may be introduced into the first mixture to form sodium hypochlorite-based compositions according to embodiments of the present disclosure. Side-sweep agitation may be used to avoid aeration while ensuring uniformity of the resultant composition. Further, while Phase A and Phase B can be prepared and combined in any suitable vessels, in some examples, Phase A and Phase B are prepared and/or combined in a vessel that does not have a metal contact surface (e.g., a non-metal vessel). Contacting the sodium hypochlorite composition with a metal surface may oxidize the metal surface, potentially reducing the efficacy of the sodium hypochlorite composition.

Sodium hypochlorite-based compositions formed using methods and/or formulations according to embodiments of the present disclosure may exhibit a pH greater than approximately 3.0 such as, e.g., a pH from approximately 3.0 to approximately 10.0, a pH from approximately 3.5 to approximately 9.8, a pH from approximately 8.5 to approximately 9.8, or a pH from approximately 8.8 to approximately 9.5. In some examples, the pH of the composition is adjusted by adding a pH adjuster (e.g., an acid or a base) to the composition. The pH of the composition may be adjusted to a range from approximately 3.5 to approximately 9.8, a range from approximately 8.5 to approximately 9.8 or any other suitable pH. For example, if the pH of composition is to high, an acidic pH adjuster such as citric acid can be added to the composition to lower the pH. Alternatively, if the pH of the composition is too low, a basic pH adjuster such as more sodium hydroxide can be added to the composition to increase the pH.

Sodium hypochlorite-based compositions formed using methods and/or formulations according to embodiments of the present disclosure may have an appearance that is clear having a light amberish color, a slight odor, and the compositions may take the form of a flowable liquid to a thick gelatinous form. In some examples, the compositions may further include additives to modify the color and/or scent of the compositions. In other examples, however, the compositions may be substantially (or entirely) free of additives that function to modify color and/or scent, as individuals using the compositions for antibacterial and/or anti-inflammatory properties may exhibit adverse reactions to such color and/or scent modifying additives. Independent of the specific additives used in a composition, a resultant composition may exhibit a viscosity from approximately 3,000 cps to approximately 50,000 cps such as, e.g., from approximately 7,500 cps to approximately 25,000 cps, or approximately 10,000 cps.

Antimicrobial and cleansing compositions in accordance with the disclosure can include a variety of different components in a variety of different concentrations, as indicated above. In one example according to the disclosure, a composition comprises (or, optionally, consist essentially of, or consist of) an antimicrobial agent (e.g., a component that includes a hypochlorite molecule), an anionic surfactant (e.g., sodium laureth sulfate), and a solvent (e.g., deionized water). In this example, the component that includes the hypochlorite molecule may form from approximately 0.025 wt % to approximately 10 wt % of the composition such as, e.g., from approximately 0.1 wt % to approximately 2 wt % of the composition, from approximately 0.15 wt % to approximately 0.75 wt % of the composition, from approximately 0.2 wt % to approximately 0.5 wt % of the composition, or from approximately 0.3 wt % to approximately 0.4 wt % of the composition. The anionic surfactant may form from approximately 3 wt % to approximately 40 wt % of the composition. The solvent can form a remainder of the composition such as from approximately 55 wt % to approximately 80 wt % of the composition. In this example, the composition may exhibit a pH from approximately 8.0 to approximately 10.0 such as, e.g., a pH from approximately 8.8 to approximately 9.5.

In another example according to the disclosure, a composition comprises (or, optionally, consist essentially of, or consist of) an alkali metal or alkaline earth metal hypochlorite (e.g., sodium hypochlorite), an anionic surfactant which may function as a foaming agent (e.g., sodium laureth sulfate), a nonionic surfactant which may function as a viscosity-enhancing agent (e.g., cocamide MEA), an amphoteric surfactant which may function to enhance foaming properties (e.g., cocamidopropyl betaine), a chelating agent (e.g., disodium EDTA or calcium disodium EDTA), and a solvent (e.g., deionized water). In this example, the alkali metal or alkaline earth metal hypochlorite may form from approximately 0.025 wt % to approximately 10 wt % of the composition such as, e.g., from approximately 0.1 wt % to approximately 2 wt % of the composition, from approximately 0.15 wt % to approximately 0.75 wt % of the composition, from approximately 0.2 wt % to approximately 0.5 wt % of the composition, or from approximately 0.3 wt % to approximately 0.4 wt % of the composition. The anionic surfactant may form from approximately 20 wt % to approximately 40 wt % of the composition such as, e.g., from approximately 25 wt % to approximately 35 wt % of the composition. The nonionic surfactant may form from approximately 1.0 wt % to approximately 7.0 wt % of the composition such as, e.g., from 3.25 wt % to 3.75 wt %, or approximately 3.5 wt %. The amphoteric surfactant may form from approximately 0.5 wt % to approximately 7.0 wt % of the composition such as, e.g., from 3.75 wt % to 4.25 wt %, or approximately 4.0 wt %. The chelating agent may form from approximately 0 wt % to approximately 2 wt % of the composition such as, e.g., from approximately 0.10 wt % to approximately 0.20 wt %. The solvent may form from approximately 55 wt % to approximately 80 wt % of the composition. The composition in this example may exhibit a pH from approximately 8.0 to approximately 10.0 such as, e.g., a pH from approximately 8.8 to approximately 9.5. Further, the composition may be substantially or entirely free of one or more (and optionally all) of the following components: sulphur resorcinol, benzoyl peroxide, salicylic acid. Alternatively the composition may include one or more of the forgoing components such as, e.g., between 0.1 wt % and 5 wt %, or between 0.4 wt % and 3 wt % salicylic acid.

Sodium hypochlorite-based compositions having antimicrobial and/or anti-inflammatory properties may be delivered to an end user in a variety of forms. Such forms may include, but are not necessarily limited to, body wash, shampoo, creams, lotions, gels, sprays, foams, pads, films, patches, towelettes, wipes, swabs, deodorants, powders, and solutions according to embodiments of the present disclosure. These compositions may be stand-alone products, for example, to cleanse wounds, treat small infections, or disinfect, among other uses. In other embodiments of the present disclosure, sodium hypochlorite-based compositions may be incorporated as a component of another product, such as deodorants or foot powders, and a lower percentage of sodium hypochlorite by weight may be employed in such compositions.

The sodium hypochlorite-based compositions may be provided in a quantity sufficient for multiple uses or a quantity sufficient for a single use. For example, the sodium hypochlorite-based composition may be provided in a single use packet. The single use packet may contain the sodium hypochlorite-based composition alone or the single use packet may contain the sodium hypochlorite-based composition in combination with another delivery agent such as, e.g., a power, lotion, wipe, towelette, or the like.

Sodium hypochlorite-based compositions that may be formed using methods according to embodiments of the present disclosure may be delivered to an end user through various mechanisms that limit exposure to heat, light and/or air prior to use. For example, the resultant composition may be loaded into sealed bottles that may be opaque in color to avoid exposing the composition to much, if any, light prior to use. Further, such sealed bottles may not include any metallic components (at least any metallic components in contact with the sodium hypochlorite-based composition) that may have a tendency to react with sodium hypochlorite or other components of the resultant composition.

Bottles or other containers that may be used to deliver sodium hypochlorite-based compositions to a user may include a self-sealing dispensing component, such as a self-sealing actuator, such that the contents of the container may be minimally exposed to light, heat and/or air until such time when the composition may be applied to the skin or another part of the body. Upon dispensing the desired amount of a sodium hypochlorite-based composition from the container, the container may reseal, thereby minimizing the amount of air that may penetrate the container. An example of an airless dispenser that may be used to hold sodium hypochlorite-based compositions according to embodiments of the present disclosure may be airless dispensers including self-sealing actuators (MegaPumps®) manufactured by MegaPlast. However, other airless dispensers and/or self-sealing actuators may be used without departing from the present disclosure. It should be appreciated that the consistency of sodium hypochlorite-based compositions according to embodiments of the present disclosure may be maintained at a viscosity such that they may delivered through a pinhole opening provided by a self-sealing actuator.

Further, as discussed above, sodium hypochlorite has a tendency to react negatively when exposed to heat. Accordingly, bottles or other containers holding sodium hypochlorite-based compositions according to embodiments of the present disclosure may be kept in cooler temperatures, at least at room temperature, in order to minimize the potential for the composition to overheat and possibly decompose and lose efficacy or strength prior to use.

Sodium hypochlorite-based compositions according to embodiments of the present disclosure may be dispensed, for example, onto a user's hand, directly onto the area of a body to be treated, or onto a cloth, such as a washcloth or a towelette, as a means to transport the composition to specified area(s) of the human body. In other embodiments of the present disclosure, the composition may be impregnated into carrier means such as a towelette or wipe. When the composition is impregnated into carrier means, the carrier means may be sealed in a container that does not react adversely with the composition prior to use and that helps prevent the composition from being exposed to light, heat and/or light prior to use.

Compositions formed according to embodiments of the present disclosure may be applied to different parts of the body as both rinse-off and/or leave-in applications. For example, such compositions may be applied to a part of a body and then be allowed to dry in place (e.g., a leave-on application, such as a lotion or cream), as it may be non-toxic to users. In other embodiments, the area to which the composition is applied may be toweled or blotted, thereby allowing the composition to evaporate or otherwise sink into the applied area. In further embodiments, the composition may be applied to an area and then rinsed off after a predetermined time. The composition may be applied with a cloth, sponge (e.g., luffa sponge), hand, or the like. In some examples, the composition may be applied by rubbing the composition onto an area (e.g., using mechanical action with a hand, sponge, or the like) for a period ranging from one second to two minutes such as, e.g., a period ranging from approximately fifteen seconds to approximately one minute. This mechanical rubbing action may help loosen and remove debris and help the composition penetrate an afflicted area.

In various examples, the composition may be applied to an area and allowed to reside on the area for greater than approximately 5 seconds before being rinsed off such as, e.g., greater than approximately 20 seconds, greater than approximately 1 minute, greater than approximately 5 minutes, greater than approximately 10 minutes, from approximately 10 seconds to approximately 5 minutes, from approximately 20 seconds to approximately 1 minute, from approximately 1 minute to approximately 2 minutes or other lengths of time, as clinically appropriate. The foregoing residence times may include the amount of time that the composition is actively rubbed on the skin of the patient (e.g., active time) and the amount of time that the composition resides on the skin of the patient without being actively rubbed (e.g., passive time).

In some applications, a user may apply the composition to a skin area larger than an area specifically targeted for treatment (e.g., an afflicted area). For example, the user may apply the composition to the skin of an entire limb that includes an area specifically targeted for treatment, to the skin of substantially the entire body (e.g., an entire body wash), or to other suitable portions of a body. Such broader application of the composition may enhance the effectiveness of the composition on the area specifically targeted for treatment, e.g., by removing sources that can re-infect or re-aggravate the area specifically targeted for treatment.

Compositions according to the disclosure may be applied to a part of the body with any suitable frequency. In some examples, the compositions may be used comparatively infrequently such as, e.g., one per month, once per week, twice per week. Alternatively, the compositions may be applied more frequently such as, e.g., at least twice per week, at least once per day, at least twice per day, or the like. In some examples, the skin of a patient may be hydrated (e.g., water wet) before applying the sodium hypochlorite-based composition, as pre-hydration of the skin may increase the effectiveness of the sodium hypochlorite-based composition.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

The following examples may provide additional details about compositions and techniques in accordance with this disclosure.

COMPOSITION DATA FOR EXAMPLES

A sodium hypochlorite-based composition was prepared for clinical testing in the following ten examples. The composition had the following components: approximately 0.3 wt % sodium hypochlorite, approximately 8 wt % sodium laureth sulfate, approximately 4 wt % cocamide MEA, approximately 7 wt % cocamidopropyl betaine, and approximately 0.1 wt % disodium EDTA. The remaining portion of the composition was made up of deionized water.

The composition was prepared by weighing out the water in a vessel and heating the water to between 70° C. and 75° C. Sodium laureth sulfate was then added while the fluid in the vessel was agitated sufficiently to produce a vortex in the vessel. While continuing to heat the fluid in the vessel, the cocamidopropyl betaine was then added and mixed until the fluid in the vessel was substantially clear and homogenous. Thereafter, the disodium EDTA was added to the fluid in the vessel as the fluid continued to be mixed and heated. Once the temperature in the vessel returned to the target range, the cocamide MEA was added to the fluid in the vessel and mixed until the fluid in the vessel was substantially clear and homogenous. At this point, the fluid was cooled down to approximately room temperature (around 30° C.). Subsequent to allowing the fluid in the vessel to cool and any air mixed into the fluid to dissipate, an aqueous sodium hypochlorite solution was added and mixed into the fluid. The resulting composition exhibited a viscosity of approximately 10,000 cps and a pH ranging from 8.8 to 9.5.

Example 1

Based on Composition Data Above

Figure 1A:
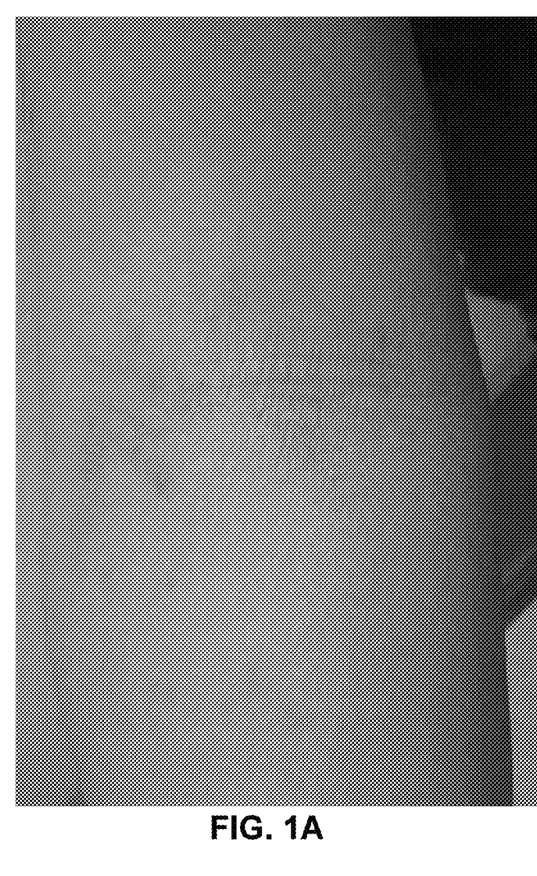
FIG. 1A is an image of an afflicted skin area of an 8 year old Caucasian female subject before being treated with a sodium hypochlorite-based composition.
Figure 1B:
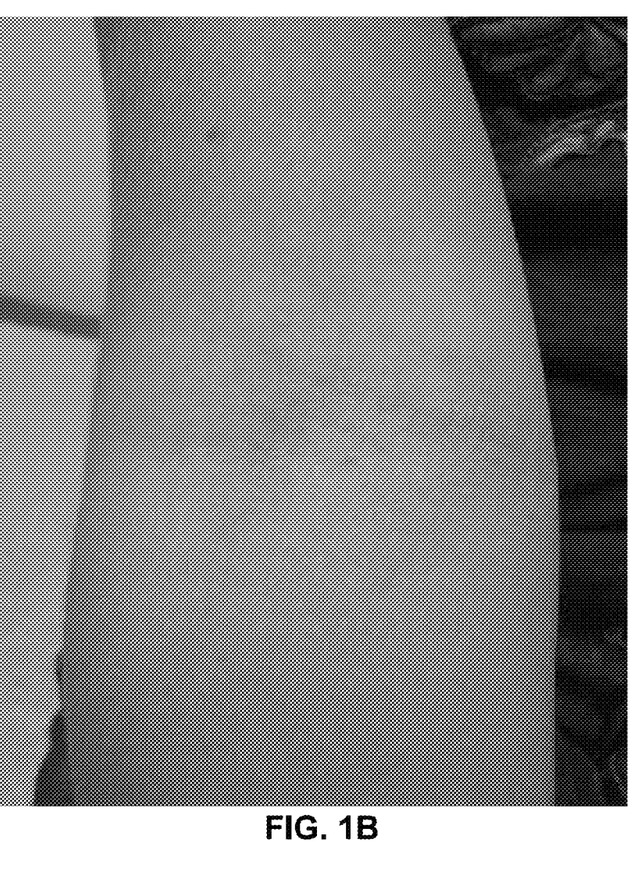
FIG. 1B is an image of the afflicted skin area of FIG. 1A after being treated with an example sodium hypochlorite-based composition according to the disclosure for four weeks.

An 8 year old Caucasian female afflicted with skin colonized with *staphylococcus aureus* was treated with the sodium hypochlorite-based composition. The subject used the sodium hypochlorite-based composition three times per week. The subject worked the composition into a lather, left the lather on her skin for approximately 30 seconds, and then rinsed the lather off with warm water. FIG. 1A shows the afflicted area of the subject before being treated with the sodium hypochlorite-based composition. FIG. 1B shows improvement in the afflicted area of the subject after being treated with the sodium hypochlorite-based composition for four weeks.

Example 2

Based on Composition Data Above

Figure 2A:
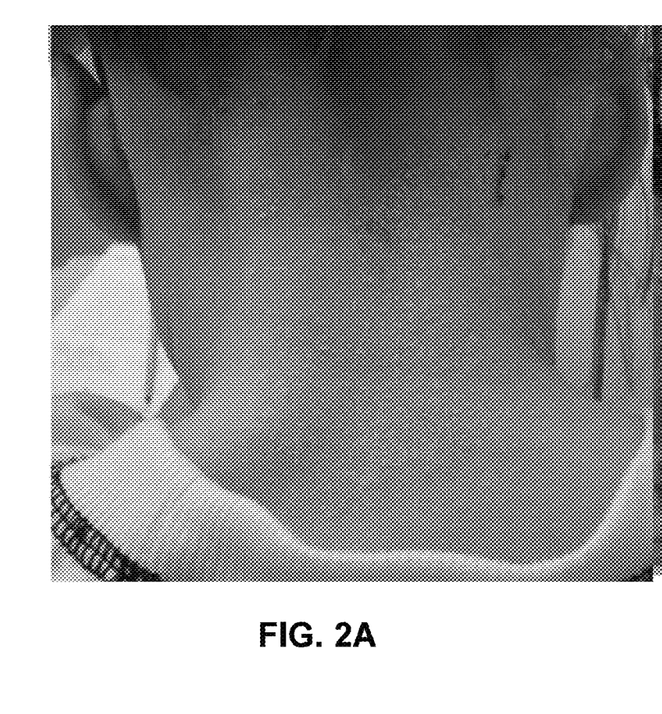
FIG. 2A is an image of an afflicted skin area of an 8 year old Caucasian female subject before being treated with an sodium hypochlorite-based composition.
Figure 2B:
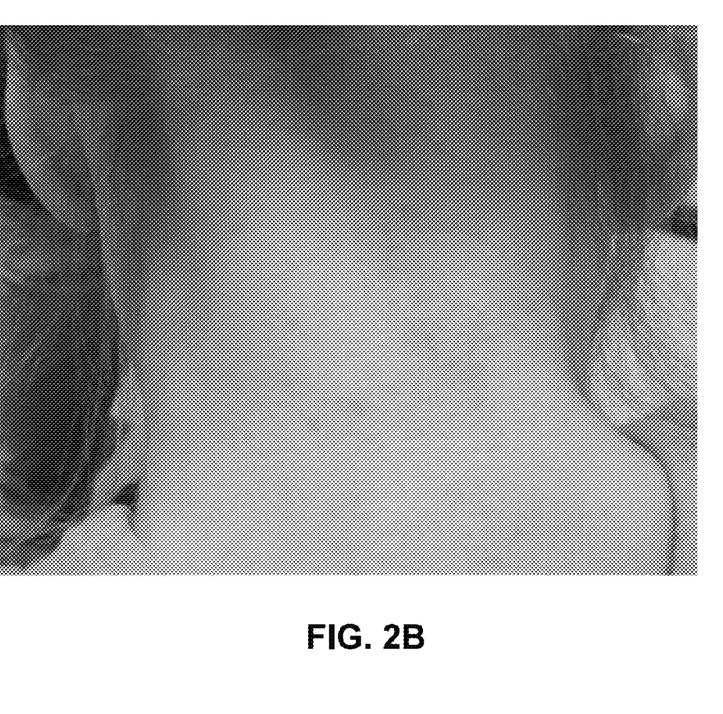
FIG. 2B is an image of the afflicted skin area of FIG. 2A after being treated with an example sodium hypochlorite-based composition according to the disclosure for two weeks.

A 7 year old Caucasian female afflicted with atopic dermatitis with severe itching was treated with the sodium hypochlorite-based composition. The subject used the sodium hypochlorite-based composition three times per week. The subject worked the composition into a lather, left the lather on her skin for approximately one minute, and then rinsed the lather off with warm water. FIG. 2A shows the afflicted area of the subject before being treated with the sodium hypochlorite-based composition. FIG. 2B shows improvement in the afflicted area of the subject after being treated with the sodium hypochlorite-based composition for two weeks.

Example 3

Based on Composition Data Above

Figure 3A:
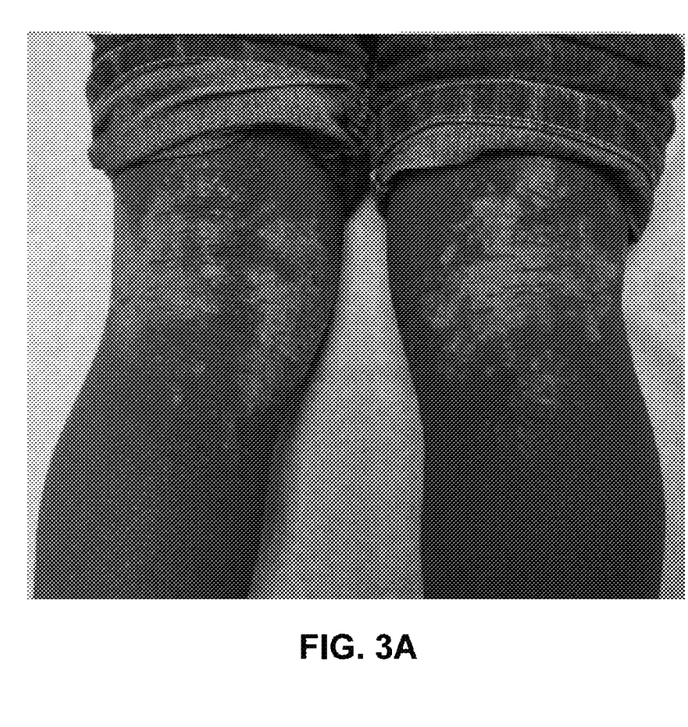
FIG. 3A is an image of an afflicted skin area of a 5 year old African American female subject before being treated with a sodium hypochlorite-based composition.
Figure 3B:
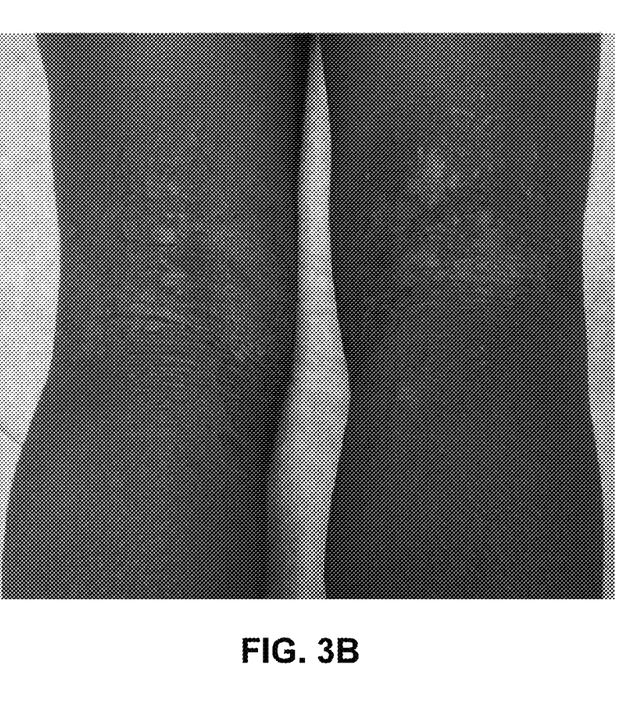
FIG. 3B is an image of the afflicted skin area of FIG. 3A after being treated with an example sodium hypochlorite-based composition according to the disclosure for two weeks.

A 5 year old African American female afflicted with an acute flare of atopic dermatitis and *staphylococcal* skin infection was treated with the sodium hypochlorite-based composition. The subject used the sodium hypochlorite-based composition three times per week. The subject worked the composition into a lather, left the lather on her skin for approximately 30 seconds, and then completely rinsed the lather off with warm water. FIG. 3A shows the afflicted area of the subject before being treated with the sodium hypochlorite-based composition. FIG. 3B shows improvement in the afflicted area of the subject after being treated with the sodium hypochlorite-based composition for two weeks.

Example 4

Based on Composition Data Above

Figure 4A:
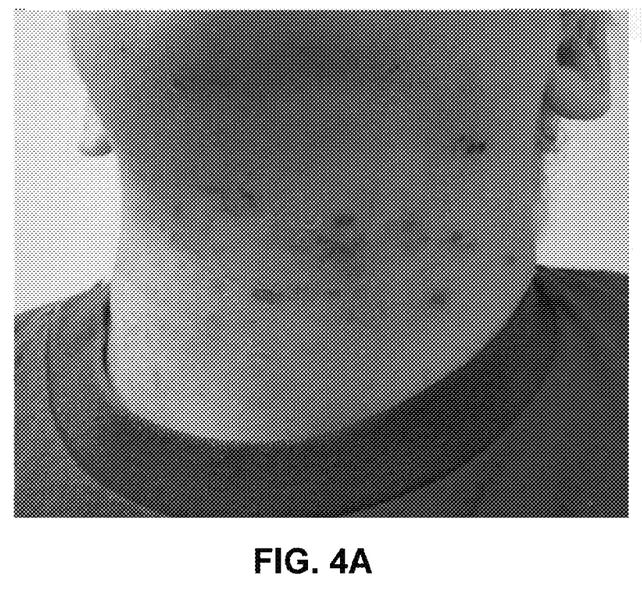
FIG. 4A is an image of an afflicted skin area of a 7 year old Caucasian male subject on an oral immunosuppressant before being treated with a sodium hypochlorite-based composition.
Figure 4B:
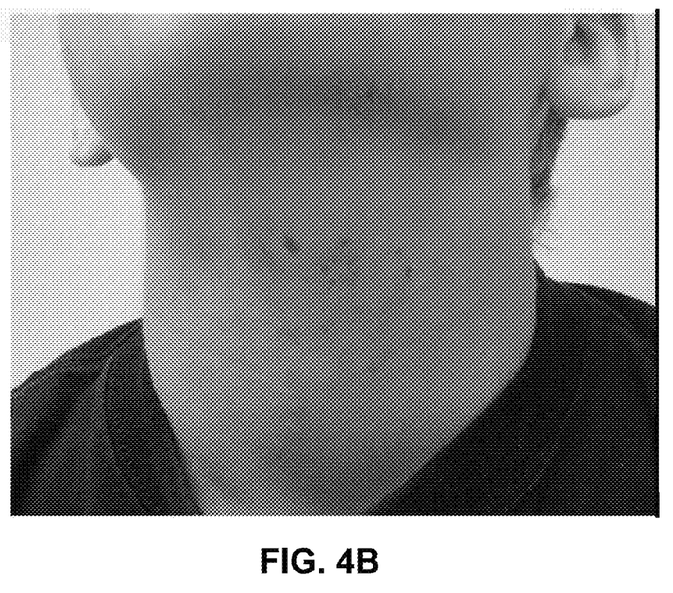
FIG. 4B is an image of the afflicted skin area of FIG. 4A after being treated with an example sodium hypochlorite-based composition for two weeks.
Figure 4C:
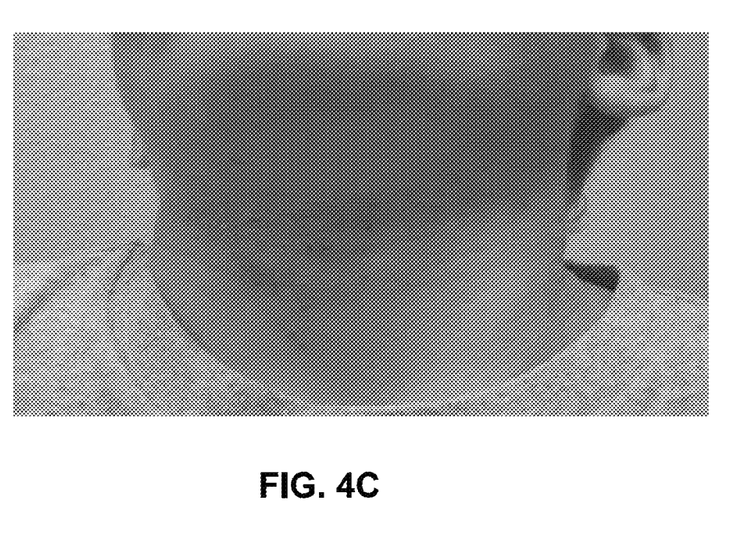
FIG. 4C is an image of the afflicted skin area of FIG. 4A after being treated with an example sodium hypochlorite-based composition for six weeks.
Figure 4D:
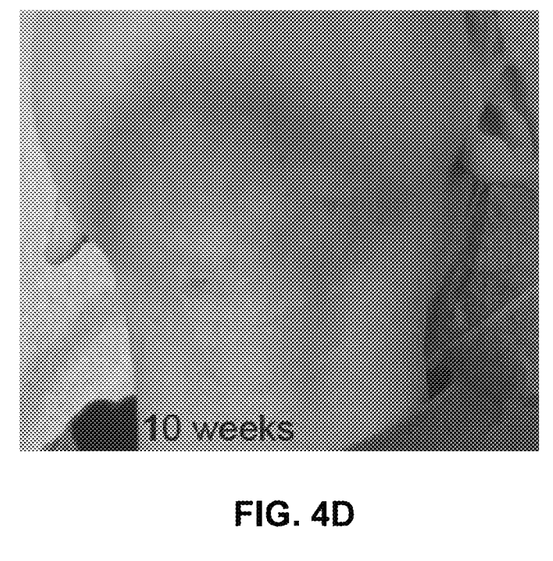
FIG. 4D is an image of the afflicted skin area of FIG. 4A after being treated with an example sodium hypochlorite-based composition for ten weeks.
Figure 4E:
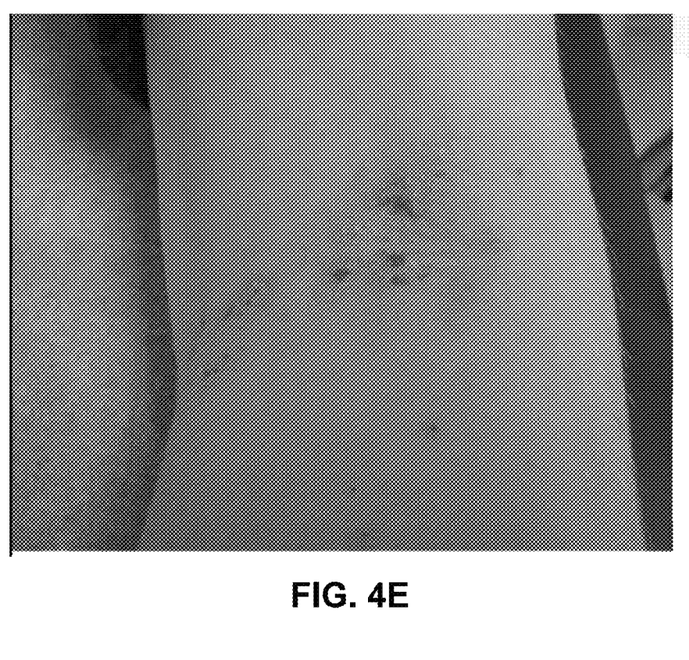
FIG. 4E is an image of a second afflicted skin area of the 7 year old Caucasian male subject of FIG. 4A before being treated with a sodium hypochlorite-based composition.
Figure 4F:
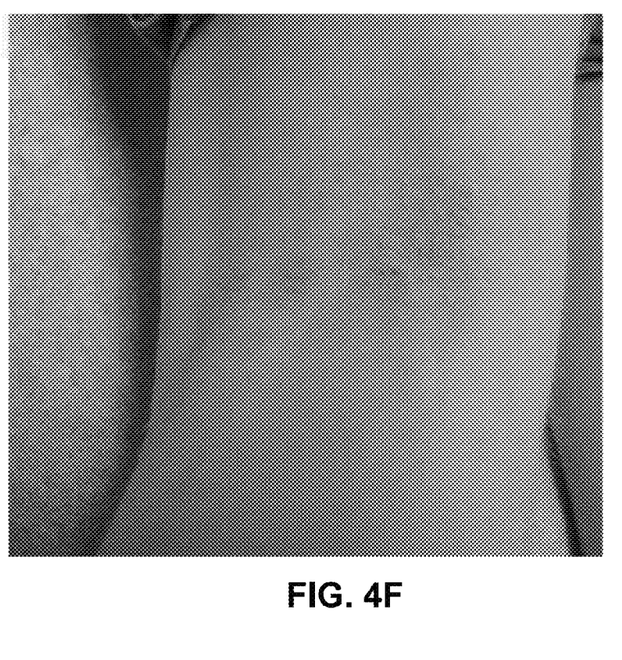
FIG. 4F is an image of the second afflicted skin area of FIG. 4E after being treated with an example sodium hypochlorite-based composition according to the disclosure for two weeks.
Figure 4G:
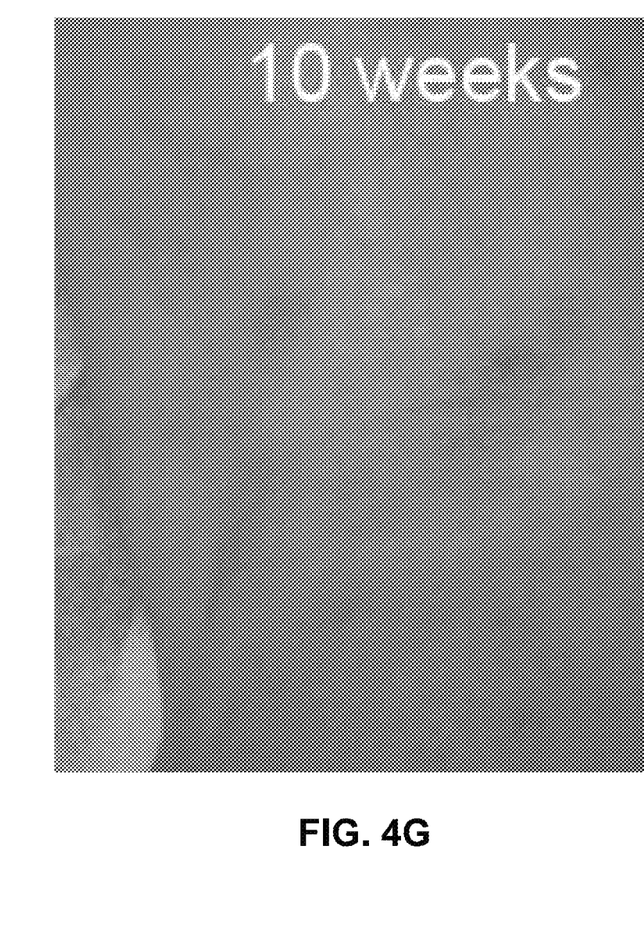
FIG. 4G is an image of the second afflicted skin area of FIG. 4E after being treated with an example sodium hypochlorite-based composition according to the disclosure for ten weeks.

A 7 year old Caucasian male on an oral immunosuppressant (cyclosporine) was afflicted with a severe acute flare of atopic dermatitis and *staphylococcal* skin infection. The subject was treated with the sodium hypochlorite-based composition. The subject used the sodium hypochlorite-based composition three times per week in the shower. The subject worked the composition into a lather, left the lather on her skin for approximately one minute, and then rinsed the lather completely off with warm water in the shower. FIG. 4A shows the afflicted area of the subject before being treated with the sodium hypochlorite-based composition. FIG. 4B shows improvement in the afflicted area of the subject after being treated with the sodium hypochlorite-based composition for two weeks. FIG. 4C shows improvement in the afflicted area of the subject after being treated with the sodium hypochlorite-based composition for six weeks. FIG. 4D shows improvement in the afflicted area of the subject after being treated with the sodium hypochlorite-based composition for ten weeks. FIG. 4E shows a second afflicted area of the same subject before being treated with the sodium hypochlorite-based composition. FIG. 4F shows improvement in the second afflicted area of the subject after being treated with the sodium hypochlorite-based composition for two weeks. FIG. 4G shows improvement in the second afflicted area of the subject after being treated with the sodium hypochlorite-based composition for ten weeks.

Example 5

Based on Composition Data Above

Figure 5A:
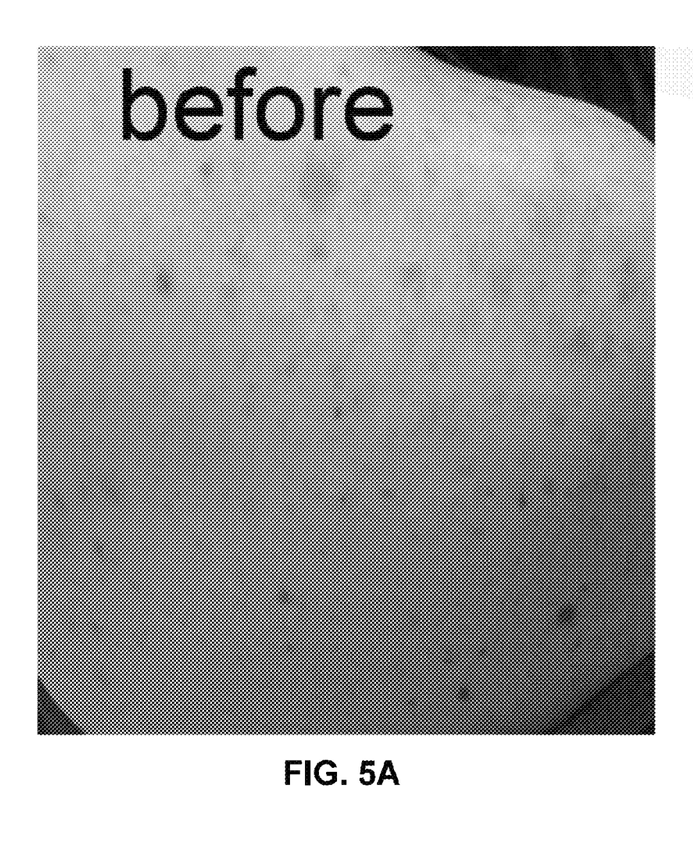
FIG. 5A is an image of an afflicted skin area of a 16 year old Caucasian female subject before being treated with a sodium hypochlorite-based composition.
Figure 5B:
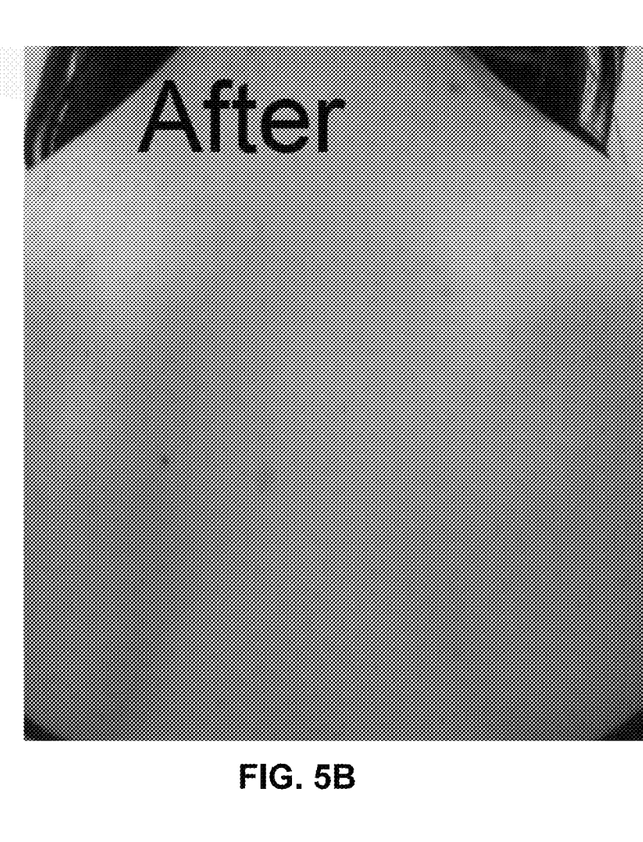
FIG. 5B is an image of the afflicted skin area of FIG. 5A after being treated with an example sodium hypochlorite-based composition according to the disclosure for four weeks.

A 16 year old Caucasian female afflicted with acne was treated with the sodium hypochlorite-based composition. The subject used the sodium hypochlorite-based composition daily as a wash. The subject worked the composition into a lather, left the lather on her skin for approximately one minute, and then completely rinsed the lather off with warm water. FIG. 5A shows the afflicted area of the subject before being treated with the sodium hypochlorite-based composition. FIG. 5B shows improvement in the afflicted area of the subject after being treated with the sodium hypochlorite-based composition for four weeks.

Example 6

Based on Composition Data Above

Figure 6A:
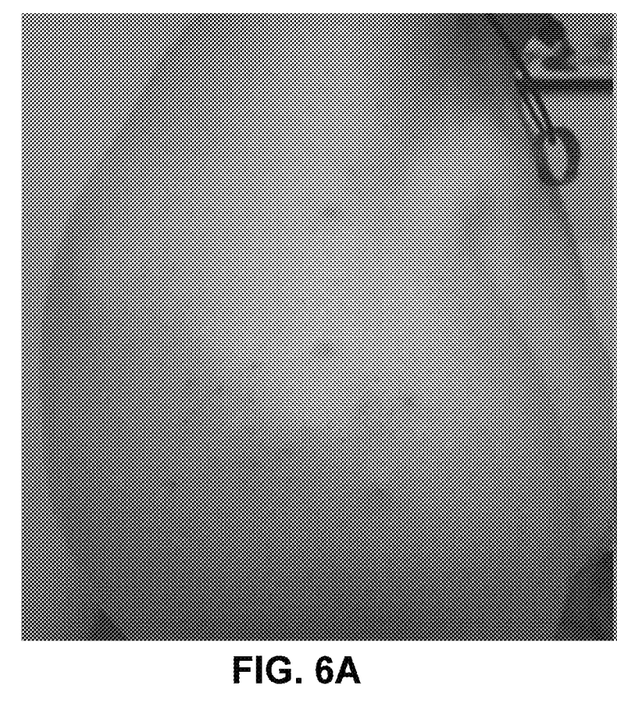
FIG. 6A is an image of a skin area of a 16 year old Caucasian female subject afflicted with acne before being treated with a sodium hypochlorite-based composition.
Figure 6B:
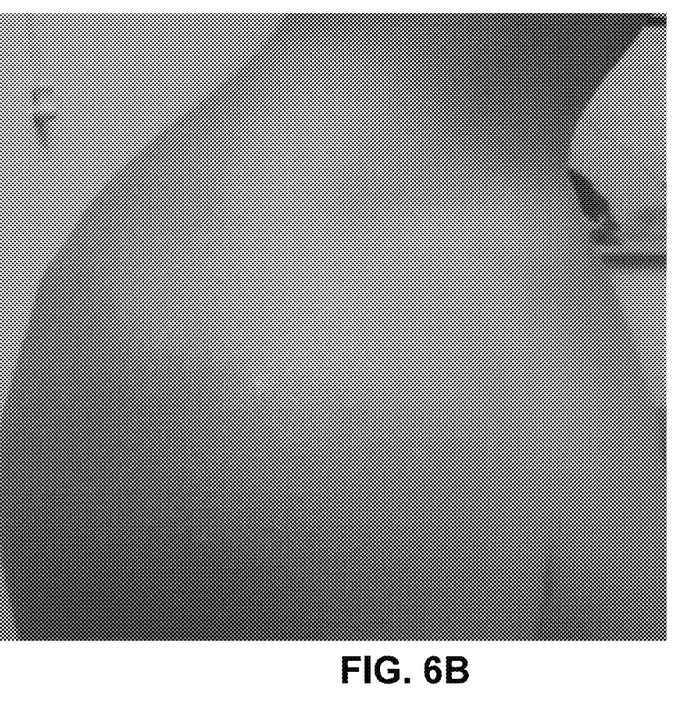
FIG. 6B is an image of the afflicted skin area of FIG. 6A after being treated with an example sodium hypochlorite-based composition according to the disclosure for six weeks.

A 16 year old Caucasian male afflicted with acne was treated with the sodium hypochlorite-based composition. The subject used the sodium hypochlorite-based composition daily. The subject worked the composition into a lather, left the lather on his skin for approximately 90 seconds, and then completely rinsed the lather off with warm water. FIG. 6A shows the afflicted area of the subject before being treated with the sodium hypochlorite-based composition. FIG. 6B shows improvement in the afflicted area of the subject after being treated with the sodium hypochlorite-based composition for six weeks.

Example 7

Based on Composition Data Above

Figure 7A:
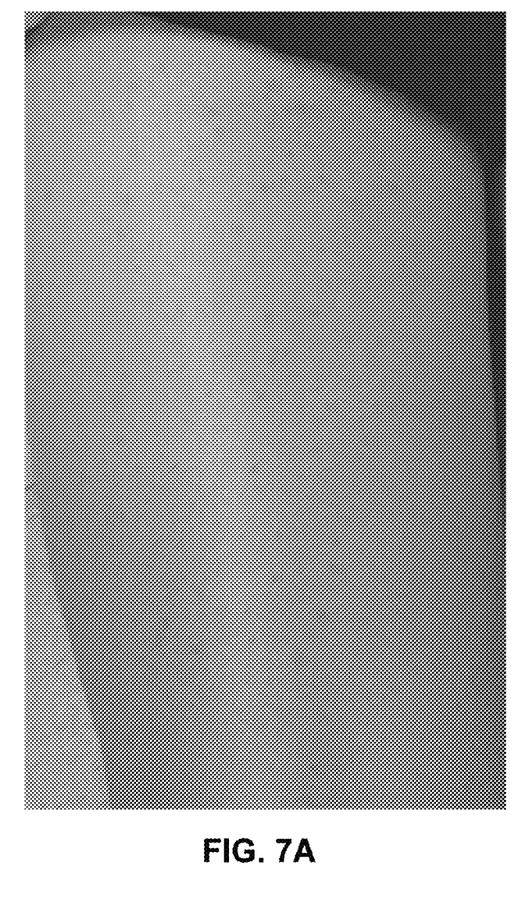
FIG. 7A is an image of an afflicted skin area of a 14 year old Caucasian female subject before being treated with a sodium hypochlorite-based composition.
Figure 7B:
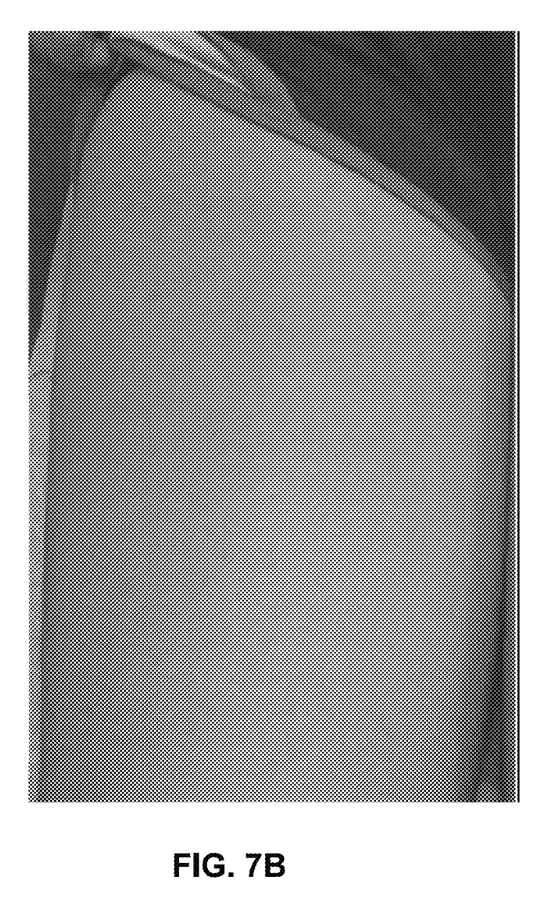
FIG. 7B is an image of the afflicted skin area of FIG. 7A after being treated with an example sodium hypochlorite-based composition according to the disclosure for five weeks.

A 14 year old Caucasian female afflicted with folliculitis was treated with the sodium hypochlorite-based composition. The subject used the sodium hypochlorite-based composition daily. The subject worked the composition into a lather, left the lather on her skin for approximately 90 seconds, and then completely rinsed the lather off with warm water. FIG. 7A shows the afflicted area of the subject before being treated with the sodium hypochlorite-based composition. FIG. 7B shows improvement in the afflicted area of the subject after being treated with the sodium hypochlorite-based composition for five weeks.

Example 8

Based on Composition Data Above

Figure 8A:
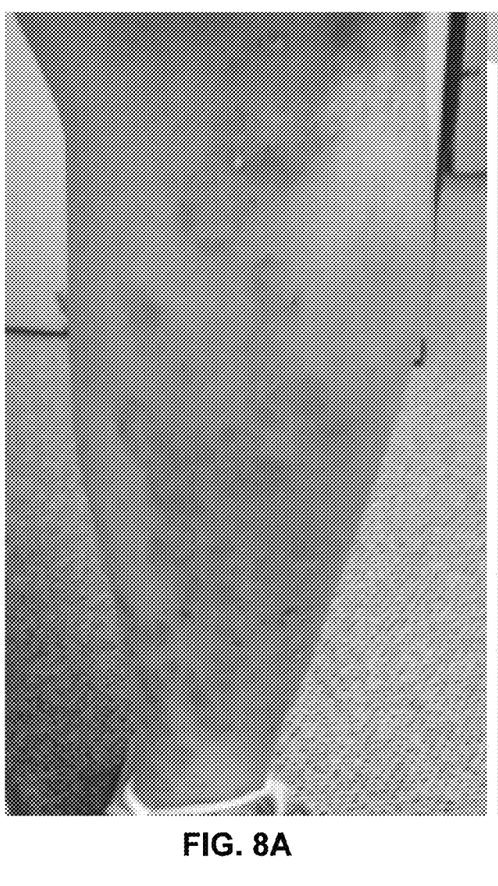
FIG. 8A is an image of an afflicted skin area of a 44 year old Caucasian female subject before being treated with a sodium hypochlorite-based composition.
Figure 8B:
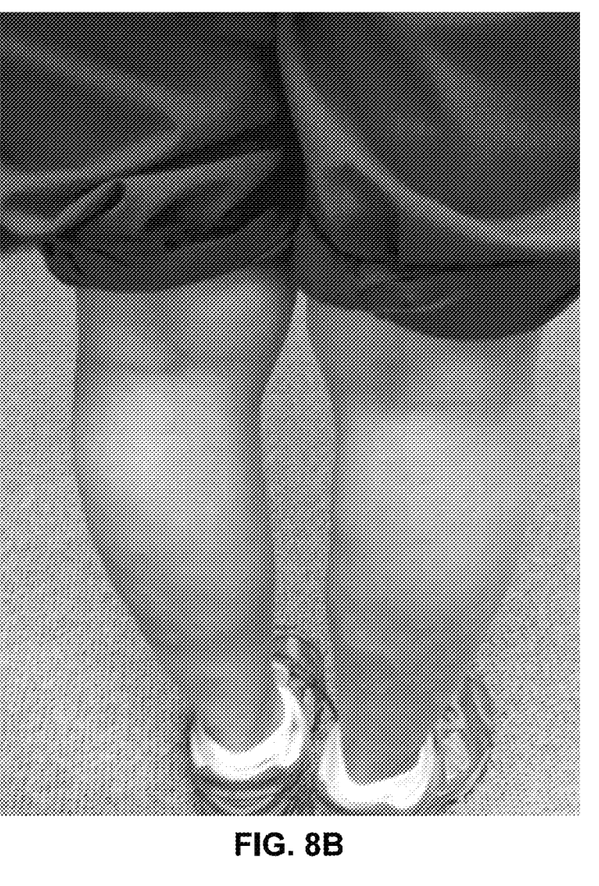
FIG. 8B is an image of the afflicted skin area of FIG. 8A after being treated with an example sodium hypochlorite-based composition according to the disclosure for six weeks.

A 44 year old Caucasian female subject afflicted with psoriasis was treated with the sodium hypochlorite-based composition. The subject used the sodium hypochlorite-based composition daily in the shower. The subject worked the composition into a lather, left the lather on their skin for approximately one minute, and then completely rinsed the lather off with warm water. FIG. 8A shows the afflicted area of the subject before being treated with the sodium hypochlorite-based composition. FIG. 8B shows improvement in the afflicted area of the subject after being treated with the sodium hypochlorite-based composition for six weeks.

The invention claimed is:

1. A body wash composition consisting of 0.1 wt % to 10 wt % of an alkali metal or alkaline earth metal hypochlorite; an anionic surfactant that functions as a foaming agent and that includes an alkyl sulfate; a nonionic surfactant that functions as a viscosity enhancing agent and that includes an alkonolamide; an amphoteric surfactant that functions as a foam boosting agent; a chelating agent and water.

2. The body wash composition of claim 1, wherein the anionic surfactant ranges from 3 wt % to 40 wt % of the body wash composition, the nonionic surfactant ranges from 1 wt % to 7 wt % of the body wash composition, the amphoteric surfactant ranges from 0.5 wt % to 7 wt % of the body wash composition, and the chelating agent ranges from approximately 0.1 wt % to 3 wt % of the body wash composition.

3. The body wash composition of claim 1, wherein the alkyl sulfate includes at least one of sodium lauryl sulfate, triethanol amine lauryl sulfate, ammonium lauryl sulfate, and sodium laureth sulfate; the alkonolamide includes at least one of cocamide monoethanolamide, cocamide diethanolamide, lauramide monoethanolamide, and lauramide diethanolamide; the amphoteric surfactant includes at least one of lauryl betaine and cocamidopropyl betaine; and the chelating agent includes at least one of EDTA, calcium disodium EDTA, disodium EDTA, trisodium EDTA, and tetrasodium EDTA.

4. The body wash composition of claim 3, wherein the alkonolamide includes cocamide monoethanolamide, the alkyl sulfate includes sodium laureth sulfate, the amphoteric surfactant includes cocamidopropyl betaine, the chelating agent includes disodium EDTA, and the alkali metal or alkaline earth metal hypochlorite includes sodium hypochlorite.

* * * * *